US006406698B1

(12) United States Patent
Svehang et al.

(10) Patent No.: US 6,406,698 B1
(45) Date of Patent: Jun. 18, 2002

(54) PHARMACEUTICAL COMPOSITION COMPRISING SERUM AMYLOID P COMPONENT FOR PROPHYLACTIC OR THERAPEUTIC TREATMENT OF VIRUS INFECTIONS AND A KIT FOR DETECTING BINDING OF COMPOSITIONS TO VIRUS COMPONENTS

(75) Inventors: Sven-Erik Svehang, Odense; Ellen Holm Nielsen, Kerteminde; Ove Andersen, Odense M, all of (DK)

(73) Assignee: Profylakse Aps, Odense NV (DK)

( * ) Notice: Subject to any disclaimer, the term of this patent is extended or adjusted under 35 U.S.C. 154(b) by 0 days.

(21) Appl. No.: 09/123,883

(22) Filed: Jul. 24, 1998

Related U.S. Application Data

(63) Continuation of application No. PCT/DK97/00035, filed on Jan. 24, 1997.

(30) Foreign Application Priority Data

Jan. 25, 1996 (DK) .............................................. 0079/96

(51) Int. Cl.$^7$ ........................ A61K 39/00; A61K 45/00; C07K 14/00
(52) U.S. Cl. ............... 424/184.1; 424/1.13; 424/278.1; 424/209.1; 530/395; 514/2; 514/8; 514/888
(58) Field of Search .......................... 424/184.1, 1.13, 424/278.1, 209.1; 530/395; 514/2, 8, 888

(56) References Cited

U.S. PATENT DOCUMENTS

| 5,221,628 A | | 6/1993 | Anderson et al. ............ 436/507 |
|---|---|---|---|
| 5,908,825 A | * | 6/1999 | Fasano et al. .................. 514/2 |
| 5,942,237 A | * | 8/1999 | Gizuardson | |

FOREIGN PATENT DOCUMENTS

WO          98-16556       *   4/1998

OTHER PUBLICATIONS

Fields et al., (Ed.) "Fields Virology", third edition, Loppincott–Raven Publishers, Philadelphia, 1996, vol. 1 pp. i–xii and 15–56.*
"Academic Press Dictionary of Science and Technology, 2001 online".*
Bristow, C.L. and R.J. Boackle, *Mol. Immunol.* 23 1045–1052, 1986.
Kubak, B.M. et al., *Mol. Immunol.* 25:851–858, 1988.
Cathcart, E.S. et al., *New Engl. J. Med.* 273:143–146, 1965.
Hawkins, P.N. et al., *J. Clin. Invest.* 86:1862–1869, 1990.
Anderson, J.K. and J.E. Mole, *Ann. N.Y. Acad. Sci.* 389:216–234, 1982.
Hess et al., *Clin. Chim. Acta* 173:331–336, 1988.
Loveless, R.W. et al., *EMBO J.* 11:813–819, 1992.
Hamazaki, H. *J. Biol. Chem.* 262:1456–1460, 1987.
Nielsen, E.H. et al., *APMIS* 102:420–426, 1994.
DeBeer, F.C. et al., *J. Exp. Med.* 154:1134–1149, 1981.

Schwalbe, R.A. et al., *J. Biol. Chem.* 266:12896–12901, 1991.
Pepys, M.B. et al., *Clin. Exp. Immunol.* 97:152–157, 1994.
Wilson, I.A. et al., *Nature* 289:366, 1981.
Couch, R.B. et al., In: Dayton, D.H. et al., (eds). The Secretory Immunologic System. Washington, D.C.:US GPO; 93, 1969.
Atkinson, W.L. et al., *Arch. Intern. Med.* 146:1751, 1986.
Wood, J. and J. Mumford. *Vet. Rec.* 126, Feb. 8, 1992.
Potempa, L.A. et al., *J. Biol. Chem.* 260:12142–12147, 1985.
Juul Sorensen, I. et al., *Int. Arch. Allergy Immunol.* 106:25–31, 1995.
DeBeer, F.C. and M.B. Pepys. *J. Immunol. Meth.* 50:17–31, 1982.
Sorensen, I.J. et al., *Scand. J. Immunology* 41:263–29.
Ada, G., *Int. Arch. Allergy Immunology* 108:304–308, 1995.
Brede, H.D., *Int. Arch. Allergy Immunol.* 108:318–320, 1995.
von Itzstein et al., *Nature* 365, 418–423, 1993.
Betts, R.F. and Douglas, R.G., In: Mandell, Douglas, Bennett (eds). Principles and practice of infections diseases. 3rd. ed., Churchill Livingstone, 1306–1325, 1990.
Webster, R.G., *Karger Gazette*, No. 57, 1–3, 1993.
Herrler, G. et al., *Virology* 141:144–147, 1985.
Niesters, H.G.M. and van der Zeijst, B.A.M., *Microbiol. Sciences* 1:55–58, 1984.
Danielsen, B. et al., *Biochim. Biophys. Acta*, in press, 1997.
Painter, R.H., *Ann. N.Y. Acad. Sci.* 389:199–215, 1982.
Dyck, R.F. et al., *J. Exp. Med.* 152:1162–1174, 1980.
Breathnach, S.M. et al., *Nature* 293:652–654, 1981.
Emsley, J. et al., *Nature* 367:338–345, 1994.
Kinoshita, C.M. et al., *Protein Sci.* 1:700–709, 1992.
Pepys, M.B. et al., *Lancet* 1:1029–1031, 1977.
Kubak, B.M. et al., *Fed. Proc.* 44:1189, 1985.
Hamazaki, H., *Biochim. Biophys. Acta* 998:231–235, 1989.
Schwalbe, R.A. et al., *J. Biol. Chem.* 265:21749–21762, 1990.
Brown, M.R. and B.E. Anderson, *J. Immunol.* 151:2087–2095, 1993.
Butler, P.J.G. et al., *J. Exp. Med.* 172:13–18, 1990.
Pepys, M.B. and Butler, P.J.G., *Biochem. Biophys. Res. Comm.* 148:308–313, 1987.
Hind, C.R.K. et al., *J. Exp. Med.* 159:1058–1069, 1994.
Sarlo, K.T., *Cell. Immunol.* 93:398–405, 1985.
Landsinann, P. et al., *Eur. J. Biochem.* 223:805–811, 1984.
Kushner, I., *Ann. N.Y. Acad. Sci.* 389:39–45, 1982.
Williams, E.C. et al., *J. Lab. Clin. Med.* 120:159–167, 1992.

* cited by examiner

*Primary Examiner*—Mary K. Zeman
(74) *Attorney, Agent, or Firm*—Darby & Darby (57) ABSTRACT

Pharmaceutical compositions comprising a protein serum amyloid P component (SAP) capable of binding viruses, especially myxovirus, e.g. influenza viruses and thereby preventing the transmission and infection with such viruses. Preferred is mucosal administration, e.g. SAP incorporated in a nose spray or nose drops. Also provided is a method for measuring the binding of SAP to the hemagglutinin of the prevailing influenza virus subtype and strain.

15 Claims, 7 Drawing Sheets

Electron microscopy of negatively stained purified human serum amyloid P component. Mag. 200.000

PHARMACEUTICAL COMPOSITION COMPRISING SERUM AMYLOID P COMPONENT FOR PROPHYLACTIC OR THERAPEUTIC TREATMENT OF VIRUS INFECTIONS AND A KIT FOR DETECTING BINDING OF COMPOSITIONS TO VIRUS COMPONENTS

This application is a continuation of International Application No. PCT/DK97/00035 filed Jan. 24, 1997, incorporated hereby by reference in its entirety.

FIELD OF INVENTION

The present invention provides pharmaceutical compositions comprising:

a) serum amyloid P component in a form capable of binding a virus component, said binding resulting in a reduction of the pathogenic properties of said virus component; and b) a physiologically acceptable carrier.

The pharmaceutical composition comprises serum amyloid P component (SAP) (a naturally occurring protein) or a binder-functional subunit thereof.

The reduction of pathogenic properties results in prophylaxis, alleviation or cure of infectious diseases caused by said virus component.

Especially preferred are compositions formulated for mucosal administration, e.g. nasal administration.

In particular, the virus component is a virus carbohydrate, e.g. exposed on a viral hemagglutinin, and the binding results in at least a partial blocking of said hemagglutinin.

The virus component may be derived from an orthomyxovirus, e.g. an influenzavirus type A, B or C from humans or animals, a virus from the paramyxoviridae family, e.g. a paramyxovirus, from a herpes virus or from a corona virus.

The invention also provides the use of serum amyloid P component (SAP) for the production of a medicament for the prophylaxis or treatment of virus infectious diseases in human beings or animals. The prophylaxis or treatment is obtained by means of SAP in a form capable of binding at least a part of a virus component causing said infectious disease, said binding resulting in a reduction of the pathogenic properties of said virus component.

According to the present invention, the serum amyloid P component (SAP) is the native protein, the recombinant protein or a binder-functional subunit thereof, the subunit being one or more complete SAP polypeptide chain(s) or a part or parts of the chain comprising the $Ca^{2+}$-dependent carbohydrate binding site(s) or synthetic peptides constructed to contain amino acid sequences contributing to said binding sites.

The infectious disease may be caused by the above-mentioned viruses.

A preferred aspect of the invention relates to a method of preventing infection with influenza virus or a parainfluenza virus and the transmission of said virus by blocking virus infectivity with serum amyloid P component (SAP). In particular, this invention relates to the prophylactic/therapeutic use of SAP in epidemics/pandemics of influenza virus infection in man.

Another aspect of the invention relates to the prophylactic/therapeutic use of SAP in epidemics/pandemics of influenza virus infection in horses, swine, and birds.

For instance for prophylactic treatment of horses the pharmaceutical composition may be contained in a vehicle for nose spray or a nebulizer, which is applied separately to the nostrils, nose or upper respiratory tract.

BACKGROUND OF THE INVENTION (HUMAN BEINGS)

Viral infections are a major cause of serious diseases for which effective prevention or treatment in many cases are still not available. The present invention is concerned with viral infections caused by the families orthomyxoviridae, paramyxoviridae, herpes viridae and corona viridae.

The orthomyxoviridae family include i.a. the orthomyxoviruses influenza viruses types A, B and influenza virus type C. Especially influenza virus type A is a major cause of morbidity and mortality due to respiratory disease, outbreaks of which may occur in world-wide epidemics.

The paramyxovirus genus comprises the four serotypes of human parainfluenza viruses, mumps virus, shipping fever virus of cattle and sheep and the avian parainfluenza virus, Newcastle disease virus. Other viruses from the paramyxoviridae family include the Morbillivirus genus (e.g. measles virus, canine distemper virus and rinderpest virus) and the pneumovirus genus (e.g. human and bovine respiratory syncytial virus). The parainfluenza viruses and respiratory syncytial virus are major pathogens causing severe respiratory tract disease in infants and young children.

The herpesviridae family comprises several important human pathogens. Important members of this family are herpes simplex types 1 and 2, varicella-zoster virus, cytomegalovirus, Epstein-Barr virus and human herpes virus type 6. The human corona viridae cause common colds and have been implicated in gastroenteritis in infants.

The main aspect of the present invention concerns human and animal influenzavirus. A more elaborate discussion of these viruses is therefore deemed proper.

Influenzavirus is a genus of viruses (family orthomyxoviridae) which includes influenza virus type A and influenza virus type B. Both A and B types cause sporadic or epidemic influenza in man; type A strains also cause epizootics in pigs, horses or birds (e.g. fowl plague and swine influenza). The viruses are transmitted via aerosols or water or by direct contact.

The enveloped virions are pleomorphic, ca. 80–120 nm in diameter. The envelope encloses the genome of 8 molecules of linear negative-sense ssRNA (total Mwt ca. $5 \times 10^6$), the RNA forming helical ribonucleoprotein complexes with protein NP. Proteins PB1, PB2 and PB3, which together constitute a transcriptase, are associated with the NP-RNA complex. The envelope is associated with viral matrix protein M1 (which occurs internally, surrounding the nucleoprotein core), M2 protein (an integral membrane protein, product of a spliced transcript of the same genome segment (1) as M1), and the glycoproteins HA (hemagglutinin) and NA (neuraminidase); HA trimers and NA tetramers form spikes and mushroom-shaped projections, respectively, which radiate from the outer surface of the viral envelope (24).

Influenza virus types are divided into subtypes (subgroups) on the basis of antigenic differences in the HA antigens (13 subtypes) and NA antigens (9 subtypes). Each individual virus strain is designated by a formula which indicates the following : type (A, B or C); the animal from which the strain was first isolated (omitted if the host was human); the place of initial isolation; the strain number; the year of isolation; and the particular HA (=H) and NA (=N) antigens. Example: A/duck/Ukraine/1/63(H3N8). In humans, strain A/Singapore/1/57(H2N2)—formerly known as "strain A2"—was responsible for the influenza pandemic of 1957 ("Asian flu"), while Strain A/Hong Kong/1/68 (H3N2) was responsible for the 1968 pandemic ("Hong Kong flu"). However, these strains are not immutable; influenza viruses undergo ANTIGENIC VARIATION in their glycoprotein antigenic determinants, allowing the viruses to overcome their hosts' immune responses and resulting in new epidemics of influenza. Two kinds of antigenic variation occur: ANTIGENIC DRIFT AND ANTI-GENIC SHIFT. Antigenic shift occurs infrequently and has been recorded only in type A strains. It appears to depend on the fact that type A strains can infect animals as well as man, and that, in mixed infections involving strains from different species, genome segments may undergo reassortment, allowing the generation of new virus subtypes (25). Since 1946, three distinct human subtypes —H1N1, H2N2 and H3N2—have arisen, each causing a new pandemic of influenza and each largely replacing its predecessor. Each prevailing subtype has also undergone regular antigenic drift (as a result of small mutational changes in HA and NA antigens), each new variant causing outbreaks and epidemics of influenza. Antigenic drift also occurs, though more slowly, in B- and C-type influenza viruses.

Influenza virus C is also a virus of the ORTHOMYX-OVIRIDAE. It is physicochemically and morphologically similar to members of the genus Influenzavirus, but differs in containing only 7 RNA segments (total Mwt ca. $4-5\times10^6$) and in having only one type of surface glycoprotein (HA) which has both haemagglutinating and receptor-destroying activities, but apparently no neuraminidase activity. It has recently been shown that, contrary to previous assumptions, sialic acid may nevertheless be an essential component of the host cell-surface receptor (26). Influenza virus C primarily infects man, although it has been isolated from pigs in China; it generally causes only mild or subclinical disease of the upper respiratory tract. Antigenic drift occurs slowly, but antigenic shift has not been observed.

Paramyxovirus is a genus of viruses of the PARAMYX-OVIRIDAE family in which the virions also have both haemagglutinin and neuraminidase activities.

The paramyxovirus virion consists of a helical nucleocapsid, composed of the genomic ssRNA and proteins NP, P and L, surrounded by an envelope containing a non-glycosylated protein (M) in the inner layer, and two glycoproteins which extend across the width of the envelope and beyond the outer surface to form spikes. Proteins P and/or L may have transcriptase activity. Protein M plays an important role in virus assembly. The larger of the envelope glycoproteins (designated HN) has cell-binding, haemagglutinating and neuraminidase activities, while the smaller (F) has haemolytic activity and promotes fusion between the virus envelope and the host plasma membrane.

Prior Art Related to Vaccination

The phenomenon of antigenic variation has made it difficult to produce effective vaccines for influenza. Attempts have been made to prepare attenuated "live" vaccines using reassortant viruses containing e.g. surface glycoprotein antigens from a currently epidemic strain. Temperature-sensitive (cold-adapted) strains have been used as the attenuated "parent", but the resulting virus tends to be genetically unstable; attempts have therefore been made to use a strain from another species with low virulence for man, e.g. avian strains. An alternative approach has been to prepare synthetic oligopeptide vaccines corresponding to the influenzavirus glycoprotein epitopes (27).

With regard to influenza A virus epidemics it is well known that even the use of a new vaccine based on the appropriate virus subtype conveys protective immunity to only 60–70% of the vaccinated population. Furthermore, only a minor part of the susceptible population is usually receiving the vaccine even in verified epidemics. In addition, due to the antigenic drift of the virus and the short duration of the specific secretory IgA antibody response, the immunity is short lasting after vaccination (14). Finally, annual vaccinations may predominantly boost antibody response directed against irrelevant strains to which the individual has once been exposed (original antigenic sin).

Prior Art Related to Specific Medicaments

Prophylaxis has been attempted with amantadine (Virofral) and the related rimantadine which are drugs for systemic use in the prevention of influenza A virus infections (15). The drugs block uncoating of influenza A virus in the host cell. However, the drugs appear ineffective in protecting household contacts from influenza as drug-resistant mutants of virus develop. In addition, the drugs may affect the central nervous system causing dizziness and insomnia. Consequently, they have found very limited application.

In conclusion, prophylactic measures against influenza A virus infections are rather inefficient as documented by the high number of individuals coming down with the disease and the over-mortality primarily due to pneumonia each time an epidemic/pandemic strikes. This in spite of continuous scientific efforts and economic investments in order to improve the vaccines and find new effective chemoprophylactic drugs.

Recently, it has been proposed that sialidase-based inhibitors might prevent influenza virus replication and therefore be used in therapeutic or prophylactic treatment (23). However, the effect has not yet been confirmed in humans.

Thus, there is a long felt need for novel and effective prophylactic measures against influenzavirus. This has been confirmed in two recent articles (21,22).

To date, attempts to develop effective vaccines against the paramyxoviruses and respiratory syncytical virus have not been successful. The drug ribavirin administrated in aerosols has been reported to be beneficial to hospitalized infants with respiratory syncytial virus infections. Effective vaccines against mumps and measles are available.

No safe and effective vaccines are available for prevention of diseases caused by the corona and herpes virus families. Antiviral compounds such as vidarabine and in particular acyclovir can alleviate the symptoms in patients with herpes virus infections.

In U.S. Pat. No. 5,221,628 A (46), a test kit for detecting or quantitating immune complexes is described. The test kit comprises a container holding SAP, said SAP being characterized in that it preferentially binds immune complexes in the presence of monomeric immunoglobulin. SAP may be bound to a solid support such as a dipstick, latex beads or a microtiter plate. In this document, it has not been suggested to add $Ca^{2+}$ in order to obtain a inhibitory effect of SAP.

BACKGROUND OF THE INVENTION
(ANIMALS)

A number of infectious diseases in animals, such as infections with influenza A virus and the parainfluenza viruses, shipping fever virus and Newcastle disease virus involve considerable problems.

Influenza has been known as the cause of epizootics of respiratory disease in equines for several centuries. It is from an economical viewpoint the most important respiratory disease in horses. Equine influenza has low mortality but high morbidity and it is spreading extremely fast. During the last decades this rapid spread of the disease has caused great economical losses to the horse owners and the equine industry (16). Similarly, outbreaks of Newcastle disease virus can inflict great economic losses on the poultry industry.

SAP is a naturally-occurring plasma protein composed of five identical subunits which are non-covalently associated in a disc-like molecule (29). SAP is also a natural constituent of glomerular basement membranes and elastic fibres of the skin and blood vessels (30, 31), the glycosylated SAP monomers have a β-pleated sheet structure and two calcium binding sites (32). The SAP molecule has been found to be resistant to proteolysis in the presence of calcium (33). Recently, the three-dimensional structure of the pentameric molecule has been solved by X-ray analysis of SAP crystals (32).

Binding of SAP to ligands is reported to include agarose, zymosan, heparin, fibronectin, the complement components C1q adn C4bp, Fab fragments of IgG and IgG aggregates (1, 10, 34–38). Furthermore, a calcium-dependent binding of sap to glycosaminoglycans, in particular heparan and dermatan sulphates, and to chromatin and DNA has been demonstrated (8, 39, 40). Both calcium-dependent binding and calcium-independent binding of SAP to amyloid AA protein and the amyloid precursor protein $\beta_2M$ globulin were described recently (28).

The best defined binding site on SAP is the one for 4,6-cyclicpyruvate acetal on β-D-galactose (41). In addition, SAP has been found to bind to mannose-rich oligosaccharide sequences and mannose-terminated sequences (2, 7).

Binding interactions with cells have also been reported. Thus, SAP was reported to bind to receptors on elicited tissue macrophages and to granulocytes (42, 43).

In humans, unlike in mice, SAP is not an acute-phase reactant (44). The physiological role of SAP is not known but it may have a function in clearance of DNA in cell death (39). An antagonistic effect of SAP on heparin's anticoagulant activities was recently reported (45).

SUMMARY OF THE INVENTION

The present invention involves use of the naturally occurring protein, serum amyloid P component (SAP).

Even though SAP has been known for many years (3), its physiological function is not known.

SAP has been isolated from man and several animal species. Very similar conserved proteins are present in all vertebrates in which they have been sought. As an example, it can be mentioned that there is a 50% homology of amino acid sequence in the N-terminal region between SAP of plaice and man. The concentration of SAP in human plasma is 30–60 μg/ml. It is synthesized in the liver and the biological half-life of human SAP is 24 hours (4). Its molecular weight is about 125 kDa and it consists of 5 subunits forming a ring (pentamer). Each subunit consists of about 205 amino acids with one intrapolypeptide disulphide bond (5). It contains 11% carbohydrate, 4% of which is galactose and mannose, 3% hexosamin and 4% sialic acid (6). SAP is highly resistant to degradation by proteolytic enzymes in the presence of calcium.

SAP has been the topic for a number of articles co-authored by the present inventors (9, 18, 20, 28), primarily concerned with its native and purified forms. The overall conclusion is that most native SAP circulates as a single pentamer, a part of which forms complexes with C4b binding protein (20). SAP shows a certain degree of heterogeneity with several isoelectric forms (18). It has an aggregation tendency, which is enhanced by $Ca^{2+}$, and during purification formation of decamers is observed (20). A pH-dependency of SAP's binding to glycosaminoglycans and amyloid proteins was demonstrated recently (28).

The present invention provides pharmaceutical compositions comprising serum amyloid P component (SAP) capable of binding myxovirus and paramyxovirus, especially influenza and parainfluenza viruses, and thereby preventing the transmission and infection with such viruses. It is believed that SAP is also effective in preventing the transmission and infection with the other viruses mentioned above. Preferred is mucosal administration, e.g. SAP incorporated in a nose spray or nose drops. Also provided is a method for measuring the binding of SAP to the hemagglutinin of the prevailing influenza virus subtype and strain.

DETAILED DESCRIPTION OF THE INVENTION

The present invention comprises a method of binding serum amyloid P component (SAP) to myxovirus especially influenza virus. The invention is based on so far unreported recognition that SAP binds selectively to oligosaccharides on the hemagglutinin molecules of different influenza virus subtypes and strains. It can be assumed that SAP also binds to oligosaccharides on cell-binding fusion glycoproteins of parainfluenza viruses.

The ability of SAP to bind influenza viruses can be utilized to inhibit or abolish the infectivity of the virus and reduce the spread of virus. To achieve this, SAP is incorporated in a nose spray or nose drops to reduce the transmission of virus produced by epithelial cells in the respiratory tract.

The invention also comprises a method of determining SAP's binding to the hemagglutinin of a prevailing influenza virus subtype and strain.

Thus, the ability of SAP to bind influenza virus may be utilized in the prophylactic/therapeutic treatment of influenza virus infections.

Without wishing to be bound by a particular molecular theory, one of the mechanisms underlying the invention may be the following:

The use of SAP according to the invention may interact with the virus components in a manner described below, taking influenza virions as an example.

Influenza A virions have 500–1000 spikes on the surface of their envelope, which mediate the attachment to the host cells. About 80–90% of these are hemagglutinins (HA) build from three monomeric subunits, the remainder being neuraminidase (NA). Each HA monomer consists of two disulphide-linked glycosylated polypeptides, HA1 with a MW of about 50 kDa and HA2 with a MW of about 28 kDa. During infection, the virions binds via the HA to sialic acid-containing glycolipid/glycoprotein surface receptors on the host cell. The sialic-binding area on the HA molecule is formed by a grove of 5–6 conserved amino acid residues. Both polypeptide chains in the HA-monomer are glycosylated with 4–6 N-glycosylation sites on the HA1 chain (up to 25% of the weight) and 1–2 on the HA2 chain (app. 6%). All carbohydrates are localized on the surface of the HA-trimer (13).

HA subtypes demonstrate varying number and localization of carbohydrate chains. These differences are due to variation in the amino acid sequence, i.e. the existence of Asn-X Ser/Thr sequences. Influenza A/Hongkong/(H3) hemagglutinins have 7 N-glycosylation sites, 6 on the HA1 chain and 1 on the HA2 chain. Five of these are oligosaccharides of complex type (GlcNAc, Man, Gal or Fuc), two are of the simple oligomannoside type (GlcNAc and Man). In comparison, influenza A/Asian (H2) hemagglutinins have 5 N-linked oligosaccharides, all of complex type, 4 on HA1 and 1 on the HA2 chain (25).

The compositions and the uses according to the present invention may be based on the following mechanisms:

Influenza virus infection is acquired by transfer of virus-containing respiratory secretions from an infected to a susceptible individual. There are large amounts of virus present in such secretions at the time of illness and virus is dispersed in small-particle aerosols produced by sneezing and coughing. A single infected individual may transmit virus to a large number of susceptible individuals. When virus reaches the respiratory tract it attaches to columnar epithelial cells and initiates a replication cycle if not blocked by specific secretory antibodies or prevented by the mucus film in the respiratory tract. The virus attaches to sialic acid on epithelial cell surface receptors via a site on the virus hemagglutinin molecule (13).

Without wishing to be bound by any particular hypothesis it can be assumed that when SAP is administered prophylactically a considerable part of the SAP molecules are bound or adsorbed on the epithelial cells so as to exhibit a protective effect against incoming virus.

In therapeutic administration the SAP molecules are brought into contact with the virions which are liberated in considerable amounts from the epithelial cells, whereby the spreading of the infection is prevented or limited. Logically, the SAP dosage used for therapeutical purposes will therefore advantageously be higher than for prophylactic administration.

Generally, infections of the respiratory tract may be caused by orthomyxoviruses or paramyxoviruses. The infection may spread to involve trachea, bronchi and the lungs. Secondary bacterial infections may occur. The incubation period is 1 to 4 days for influenza virus infections and 1 to 7 days for parainfluenza virus infections. To prevent transmission of virus by virus-carrying small-particle aerosols the pharmaceutical composition according to the invention is administered as early as possible during an epidemic or local outbreak of the respiratory virus disease.

According to an aspect of the invention compositions comprising SAP and a specific amount of $Ca^{2+}$ may be used. A preferred amount of $Ca^{2+}$ is a final concentration corresponding to the physiological amount, viz. 1.2–1.5 mM.

SAP exhibits $Ca^{2+}$-dependent binding to certain carbohydrates. SAP has been shown to bind to zymosan, agarose and other polysaccharides (17) and to mannose-terminated sequences of polysaccharides and glycoproteins (2). However, its binding to influenza virus components has not been described earlier. SAP has the capacity of multispecific $Ca^{2+}$-dependent binding to oligosaccharides with terminal N-acetylgalactosamin, glucuronic acid, 6-phosphate-mannose and to certain glycosaminoglycans (7, 8, 9, 10). It has also been reported to bind $Ca^{2+}$-dependently to heparin, fibronectin, C1q,C4b-binding protein (C4bp) and chromatin (1, 11, 12). Some authors (11) propose that nearly all SAP in the blood is bound to C4bp. In the presence of $Ca^{2+}$, human IgG and Fab, but not Fc were found to bind to SAP (1).

Besides of the active SAP the pharmaceutical compositions according to the invention also comprise a pharmaceutically acceptable carrier. Obviously, said carrier will depend on the chosen mode of administration and may comprise usual preservation agents, such as p-hydroxy benzoate, and/or stabilizers.

The presently preferred formulation is a nasal spray which may be formulated in aqueous solution and packed into spray containers either with an aerosol or provided with means for manual compression.

A preferred embodiment of a nasal spray comprises SAP in an amount of at least 50 µg/ml in isotonic NaCl, $CaCl_2$ at about the physiological level (1.2–1.5 mM) and further comprising a viscosity enhancing factor, so as to prolong the contact with the mucous membrane. It is assumed that with a spray dosis of $\geq 50$ µg, 1–2 sprays, 2–4 times per day in each nostril is sufficient for prophylactic purposes.

The composition may also be administered in the form of nose drops having the same composition as the spray except for the propellant, and presumably having a higher concentration of SAP. It is assumed that 2–4 drops, 2–3 times per day in each nostril is sufficient for prophylactic purpose.

In both cases the dosage for therapeutic purposes will depend on the severity of the infection and will be determined in consultation with the responsible physician.

The composition may also be formulated as a nasal ointment.

DETAILED DESCRIPTION OF THE PRESENTLY PREFERRED EMBODIMENTS

Native SAP may be isolated by a combination of different purification methods (17, 18, 19). We have preferred affinity chromatography on Sepharose or DNA-agarose combined with anion-exchange chromatography, and for some preparations, a final affinity chromatography on Protein G-Sepharose. The method of preparing SAP is described in further detail below in Example 1. Modifications of this procedure for isolating native SAP may also be used.

The purity of the isolated SAP preparation is analyzed by SDS-polyacrylamide gel electrophoresis, Western blotting and electron microscopy. This characterization of isolated SAP may be supplemented by other methods for analyzing the purity of protein preparations.

According to the present invention, the so isolated SAP or SAP produced by recombinant techniques may be utilized to bind influenza virus and prevent transmission of and infection with the virus. Subunits/Peptides of SAP can be prepared which may have the necessary biological functionality and the invention also comprises the use of such subunits/peptides that bind influenza virus and inhibit virus infectivity.

In particular subunits of SAP comprising one or more complete SAP polypeptide chain(s) or a part or parts of the chain comprising the $Ca^{++}$ dependent carbohydrate binding site(s) can be prepared or synthetic peptides constructed to contain amino acid sequences contributing to said binding sites may be used.

With respect to bringing SAP in contact with the virus in infected individuals, SAP in liquid phase containing $Ca^{++}$ is incorporated into a vehicle for nose drops, nose spray or a nebulizer and the drops or spray are applied to the nose or upper respiratory tract. In this way influenza virus released from infected columnar epithelial cells becomes coated with SAP molecules that bind preferentially to the virus hemagglutinin. This inhibits the local spread of virus to other epithelial cells as well as the transmission of virus via small-particle aerosols to other susceptible individuals.

With respect to preventing the transmission of influenza virus to susceptible but not infected individuals SAP is brought in contact with the virus by application of SAP-containing drops or spray to these individuals as described above. The virus-carrying small-+particle aerosols produced by influenza virus infected individuals will in this way come in contact with fluid phase SAP that inhibits the infectivity of the virus before it reaches the epithelial cells in the upper respiratory tract.

A test kit for determining the binding of SAP to the prevailing influenza virus strain is also part of the present invention. The kit comprises a container holding a solution of SAP and a container with indicator cells.

The invention further comprises a method of detecting or measuring the binding of SAP to the prevailing influenza virus strain in an epidemic. Purified native SAP or recombinant SAP and buffer only are incubated with the virus isolate, dilution series are prepared and indicator cells are added. The ability of SAP to inhibit the virus hemagglutination reaction can now be determined by comparing the hemagglutination titer in the two dilution series. Alternatively, the binding of SAP to influenza virus can be detected by conventional immunoassays, including radioimmunoassay, enzyme immunoassays and fluorescence assays. The performance of these assays is known to those skilled in the art.

EXAMPLES

The invention is further illustrated by the following examples.

Example 1

Hemagglutination inhibition (HI) tests were performed to compare the binding of different SAP preparations to several different influenza A virus strains.

SAP was isolated from normal human blood plasma by a standard procedure previously described (see Ref. 18). The citrated plasma was stored at −80° C., thawed at 4° C. and recalcified to 20 mM $CaCl_2$. The serum (200 ml) was centrifuged at 3.000 g and 4° C. for 10 min, diluted 1:1 in 100 mM Tris, 150 mM NaCl (TBS) containing 2 mM $CaCl_2$, pH 7.4, and applied to a Sepharose-4B-Cl column, at 4° C., with a bed volume of 162 ml and a flow rate of 0.5 ml/min. The column was washed with the loading buffer until the absorbance at 280 nm was less than 0.001. Bound proteins were eluted with TBS containing 2 mM EDTA, pH 7.4. In some purifications 0.5 mM cyclokapron, 0.5 mM iodoacetamide and 0.5 mM PMSF, final concentrations were added to the Sepharose eluate. The protein-containing fractions were pooled and dialyzed against 10 mM Tris, pH 7.4, before further purification and characterization by anion-exchange chromatography on a MA7Q column (Bio-Rad, Richmond, Calif., USA) (bed volume 3.5 ml) using the Pharmacia FPLC system. Elution was performed with a 0–1 M NaCl gradient for 60 min in 10 mM Tris, pH 7.4. The flow rate was 1 ml/min and 0.5 ml fractions were collected. The protein concentration of SAP preparations was measured by UV absorption using $E_{280}=1.84$.

Figure 1:
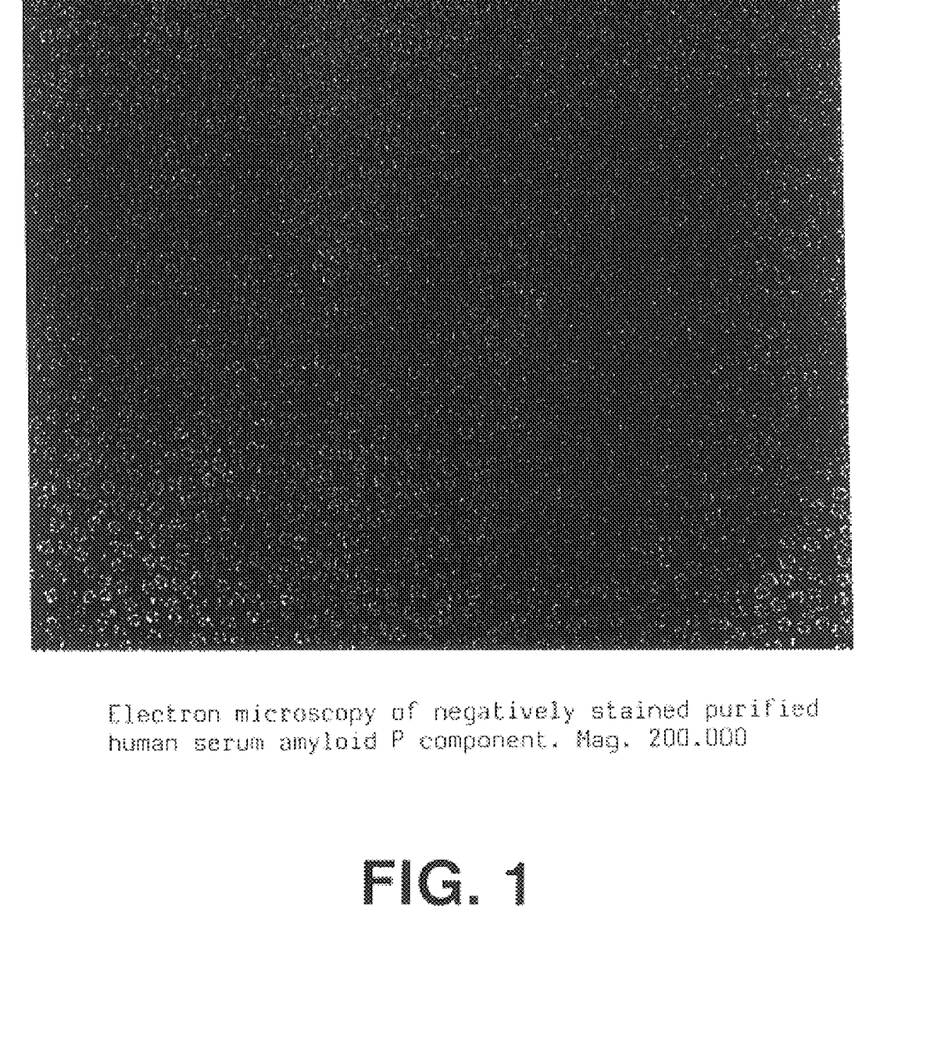
FIG. 1 shows an electron microscopy of negatively stained purified human serum amyloid P component. Mag. 200.000.

The purity of SAP in the peak fractions from the anion exchange column was estimated by SDS polyacrylamide gel (4–20%) electrophoresis developed with silver nitrate, by Western blotting, performed as described previously and by electron microscopy (FIG. 1). The SAP may be further purified by passage through a Protein G-column which removes traces of immunoglobulins.

For hemagglutination inhibition assay (HI) microtiter plates with round-bottomed wells (Nunc) were used. SAP is diluted in TBS containing 1 mM $Ca^{++}$ to a final concentration of 3.2 µg/ml and 50 µl is transferred to the first well. From this well a two-fold dilution series in TBS+1 mM $Ca^{++}$ is prepared. To all wells is added 50 µl virus (whole or HA subunits) containing 4 HA units of virus. The 4 HA units have been determined in a HA test. The microtiter plate is incubated for 30 min at 20° C. with slow agitation. Washed chicken erythrocytes or human type 0,Rh- erythrocytes (50 µl, 1.5% suspension) are added to all wells and the plate is incubated for 30 min at 33° C. The lowest concentration of SAP which inhibits the HA reaction is determined by visual inspection of the plates.

Figure 2:
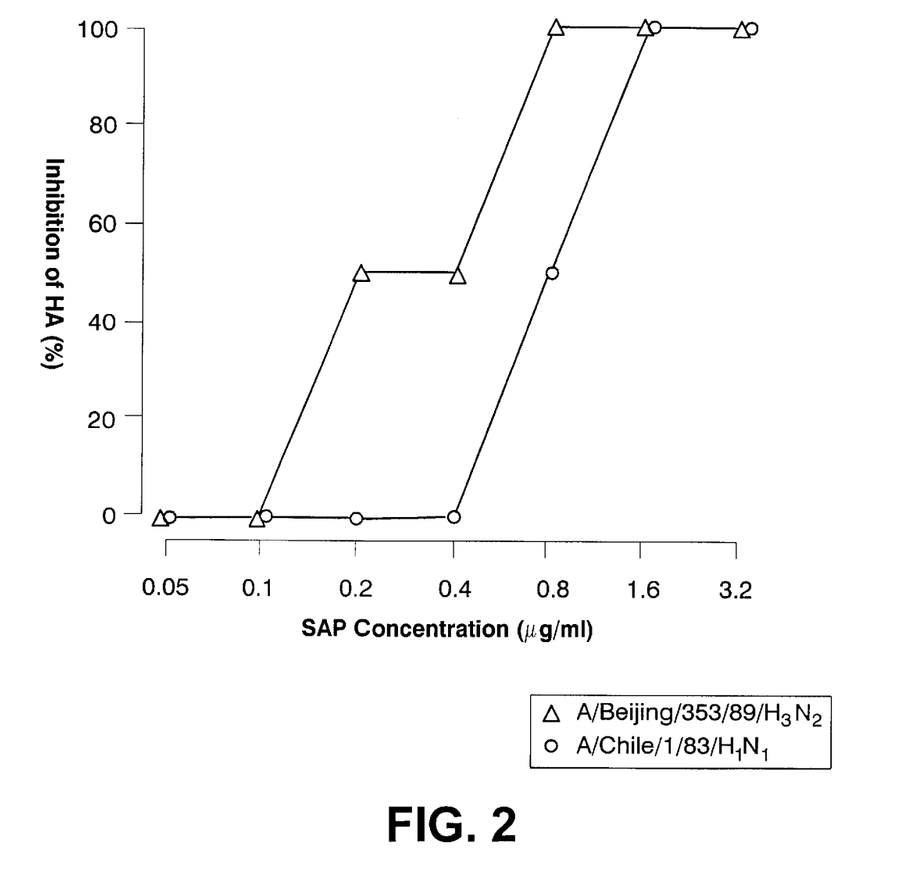
FIG. 2 shows the dose-response inhibition of virus hemagglutination (HA) when two different influenza virus A strains were preincubated with increasing concentrations of human SAP.

The results obtained with two different influenza A virus strains are shown in FIG. 2. Total inhibition of virus HA was seen when virus was incubated with 0.8–1.6 µg SAP/ml.

Figure 3:
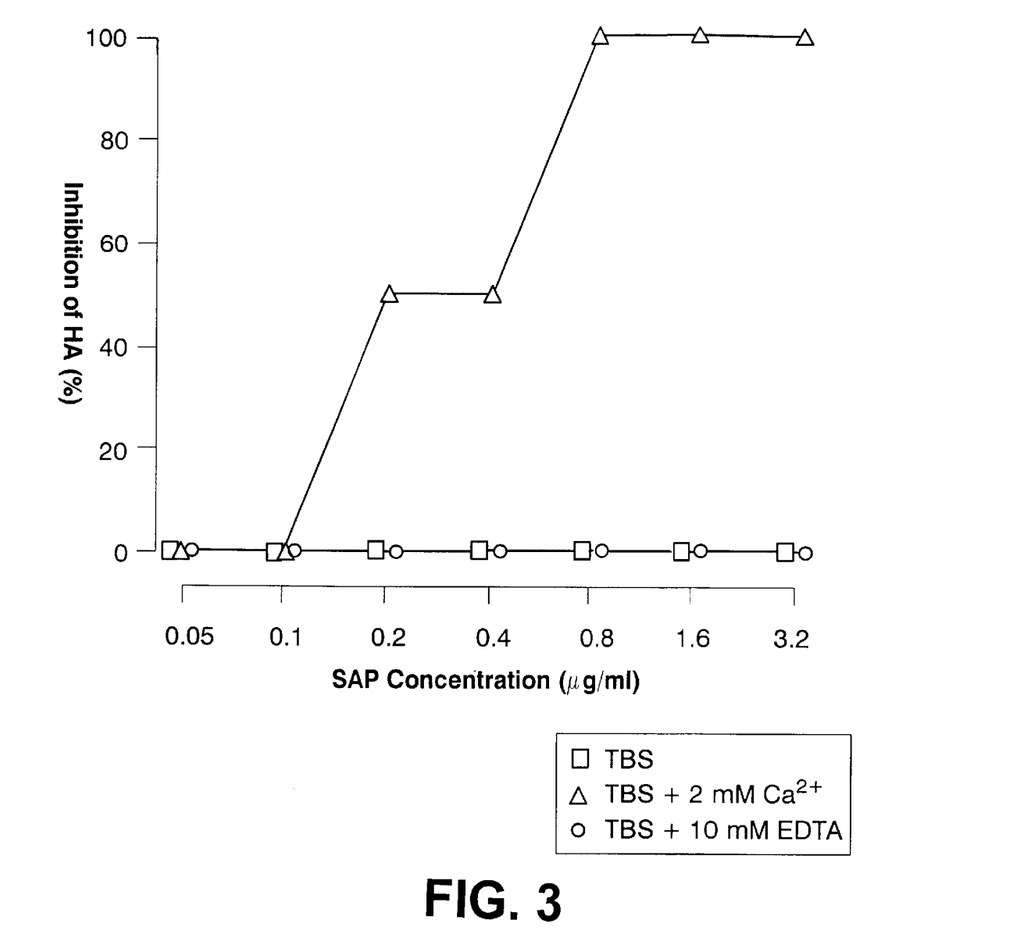
FIG. 3 shows that the SAP-mediated inhibition of influenza A virus hemagglutination (HA) is $Ca^{++}$-dependent.

For studying the influence of $Ca^{++}$ on the binding of SAP to influenza A virus, SAP was diluted in TBS without $Ca^{++}$ or with the addition of $Ca^{++}$ at different concentrations or with addition of EDTA (10 mM). The HI test was then performed as described above. The inhibitory effect of SAP on virus HA is $Ca^{++}$-dependent (FIG. 3) and no inhibition is seen in the absence of $Ca^{++}$. Other data have shown that physiological levels of $Ca^{++}$ (1.2–1.5 mM) are sufficient for optimal inhibition of virus HA by SAP.

Figure 4:
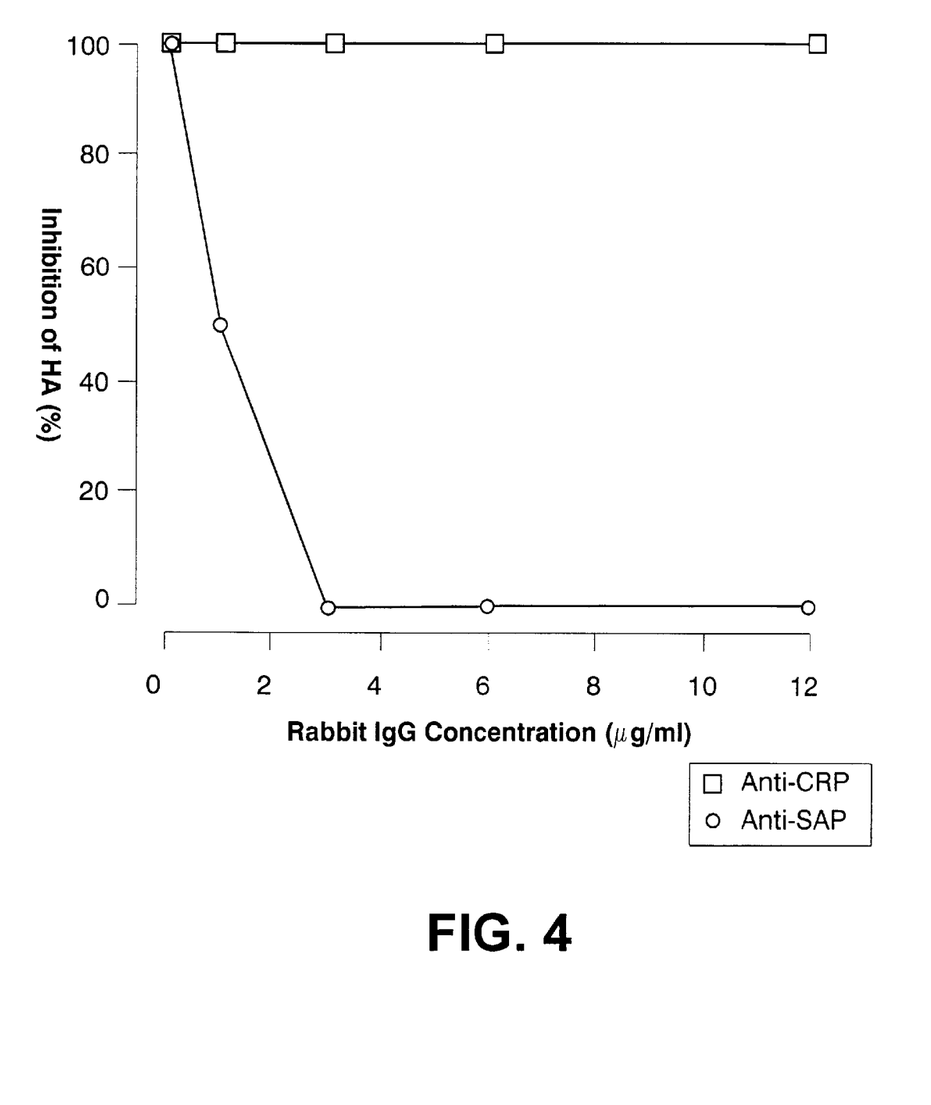
FIG. 4 shows that polyclonal rabbit antibodies against human SAP abolished the SAP-mediated inhibition of influenza A virus hemagglutination. Polyclonal antibodies against C-reactive protein had no effect on the inhibition exerted by SAP.

To determine whether specific polyclonal antibodies to SAP were able to interfere with or abolish the HI activity of SAP, SAP preparations were preincubated for 30 min at 20° C. with increasing antibody concentrations. Polyclonal antibodies against C-reactive protein were used as control. The HI test was then performed as described above. The results (FIG. 4) show that polyclonal antibodies against SAP abolished the SAP-mediated inhibition of virus HA. Antibodies against other serum proteins exerted no influence on SAP's binding to the influenza virus.

HI tests were also performed to determine whether monosaccharides or glycosaminoglycans would influence the HI activity of SAP. SAP was diluted in TBS with 2 mM $Ca^{++}$ and preincubated for 30 min at 20° C. with 10 mM monosaccharides or 50 μg/ml glycosaminoglycans. The HI test was then performed as above. Both heparin, heparan sulphate and D-mannose reduced, but did not abolish the antiviral activity of SAP. Heparin is known to bind with high affinity to SAP and the effect of this glycan was most pronounced.

To investigate whether denaturated and renaturated SAP would show HI activity two treatments were compared. One treatment comprised the reduction of SAP (1.0 mg/ml) with 1,4-Dithio-L-threitol (0.15 M) for 2 h at 20° C. followed by dialysis for 2 h at 20° C. against TBS. A control SAP sample was treated in the same way with the exception that Dithio-L-threitol was replaced by TBS. The HI test, performed as described above, showed that 1 to 2 μg/ml of the reduced and dialyzed SAP inhibited the HA reaction. The control SAP preparation showed the same inhibitory activity at 0.5–1 μg SAP/ml.

The second type of treatment was exposure of SAP (1.0 mg/ml) to pH 4.0 (0.1 M HCl) for 30 min at 20° C. followed by gradual titration with 0.1 M NaOH for 30 min back to pH 7.4. A control SAP preparation was incubated at 20° C. for 1 h. The HI test, performed as described above, showed that SAP's inhibitory activity was not reduced by the treatment as 0.6 μg SAP/ml of both preparations was sufficient to abolish the HA reaction.

To illustrate that SAP could inhibit different strains and subtypes of influenza A virus 10 different strains were tested. It is shown in Table 1 that human SAP (0.2–3.2 μg/ml) inhibited the HA reaction of nine of the strains. It is not known whether also the 10th strain (A/Mississippi/1/85/H3N2) would have been inhibited with a SAP concentration exceeding 3.2 μg/ml.

TABLE 1

| Strain | Subtype | Inhibition of HA reaction by SAP[1] |
| --- | --- | --- |
| A/Taiwan/1/86 | H1N1 | + |
| A/Beijing/353/89 | H3N2 | + |
| A/Singapore/6/86 | H1N1 | + |
| A/Beijing/32/92 | H3N2 | + |
| A/Chile/1/83 | H1N1 | + |
| A/Mississippi/1/85 | H3N2 | —[2] |
| A/Shangdong/9/93 | H3N2 | + |
| A/Copenhagen/5/92 | H3N2 | + |
| A/equine/Miami | H2N2 | + |
| A2/equine/Fontainebleau | H2N2 | + |

[1]Inhibition using 4 HA units of virus and 0.2–3.2 μg human SAP/ml
[2]SAP concentrations exceeding 3.2 μg/ml were not tested Example 2

The procedure when the effect of SAP on virus replication and HA production in cell cultures is investigated is to preincubate the virus suspension with from 0 to 40 μg/ml of sterile filtered SAP for 30 min at room temperature before inoculation of the cultures. After 24, 48 and 72 hrs., 50 μl of the culture medium from infected cultures and control cultures is transferred to the first well (containing 50 μl physiological NaCl) of a microtiter plate and a two-fold dilution series is made in NaCl. Chicken erythrocytes (50 μl, 1.5% suspension) are added to all wells, the plate is incubated for 30 min at 33° C. and the HA titer is read by visual inspection of the plate.

To demonstrate the effect of SAP on influenza A virus infection of cell cultures MDCK-cells (American Type Culture Collection) were used. Purified, sterile filtered SAP, 0–150 μg/ml, and influenza A virus/Shangdong/9/93 (H3N2) and Taiwan/1/86 (H1N1) are preincubated for 30 min at room temperature. MDCK-cells are grown at 37° C. to near confluency in chamber slides (Nunc) in BME-medium with 4% fetal calf serum with 1% Glutamax and 1% Gentamycin. The cells are washed with serum-free medium whereafter 2 ng/ml trypsin are added to the SAP-virus mixture and 100 μl of this are transferred to the cells. After incubation for 2 h at 33° C. in 5% $CO_2$, serum-free medium with trypsin-$CaCl_2$ is added to a total volume of 1 ml. The cells are incubated for 3 days at 33° C. with 5% $CO_2$. Every day HA tests are performed on the culture medium, the cytopathogenic effect is read in the microscope and the cell cultures are photographed. On the third day the slides are immunostained with FITC-conjugated monoclonal antibodies to influenza A virus antigens (DAKO).

Controls cultures without SAP and without virus and SAP are included.

To illustrate the effect of polyclonal anti-SAP antibodies on the virus inhibiting activity of SAP, rabbit antibodies against human P-component (DAKO) were incubated with SAP for 24 hours at 4° C. before performing experiments as described above.

The effect of SAP on production of the two influenza A virus subtypes in MDCK-cells is shown in Table 2. Using SAP concentrations exceeding 10–20 μg/100 μl no detectable virus hemagglutinin was produced whereas the HA titer of medium from control virus cultures was 64–128.

TABLE 2

| | SAP concentration (μg/100 μl) | | | | SAP (20 μg/100 μl) + anti-SAP |
| --- | --- | --- | --- | --- | --- |
| HA titer[1] | 64–128 | ≤–4 | >4 | >4 | 64–128 |
| Cytopathogenic effect[2] | 3+ | (+) | – | – | 3+ |
| Immunofluorescence[2] | 3+ | + | (+) | (+) | 3+ |

[1]Virus inoculum for MDCK-cells: 32–64 HA units
[2]3+, pronounced cytopathogenic effect, all cells showing positive immunofluorescence; +, scattered single cells showing weak immunofluorescence.

Figure 5A:
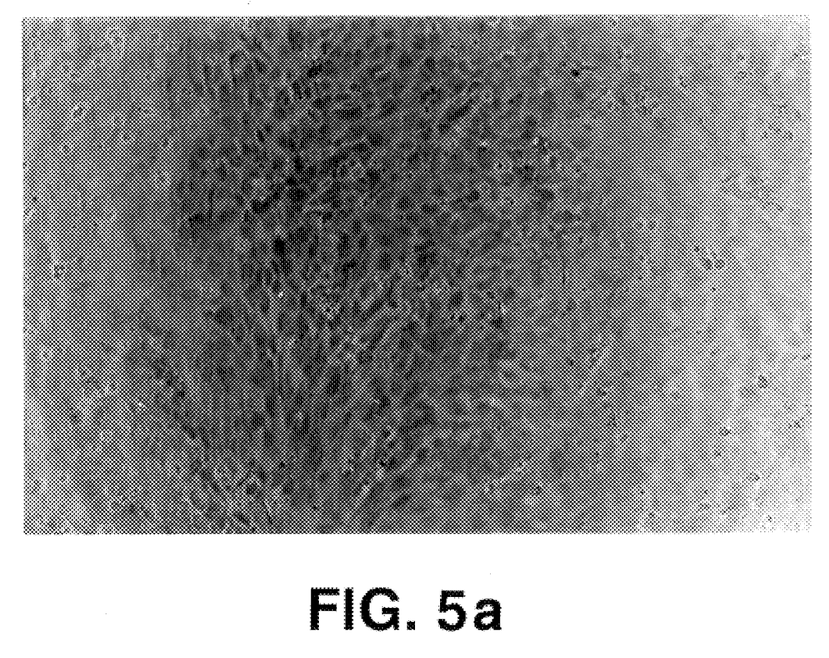
FIG. 5 shows that SAP protected MDCK cells from infection with influenza A Shangdong 9/93 (H3N2) virus. a) MDCK cells plus virus (2 HA units) and SAP (15 μg/100 μl), b) MDCK cells and virus and c) MDCK cells only. The photos were taken on the third day after infection of the cultures. Magn. 250×.
Figure 5B:
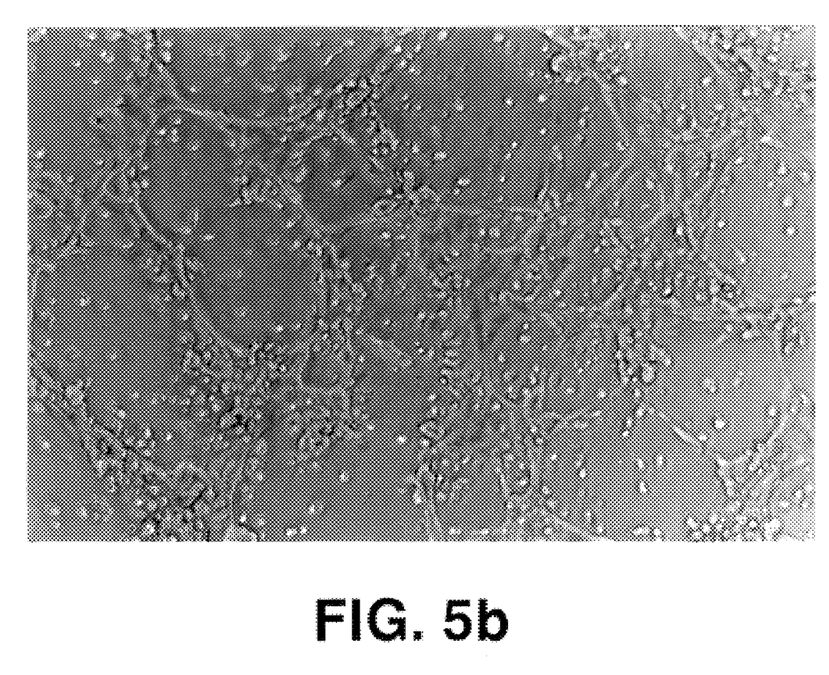
Figure 5C:
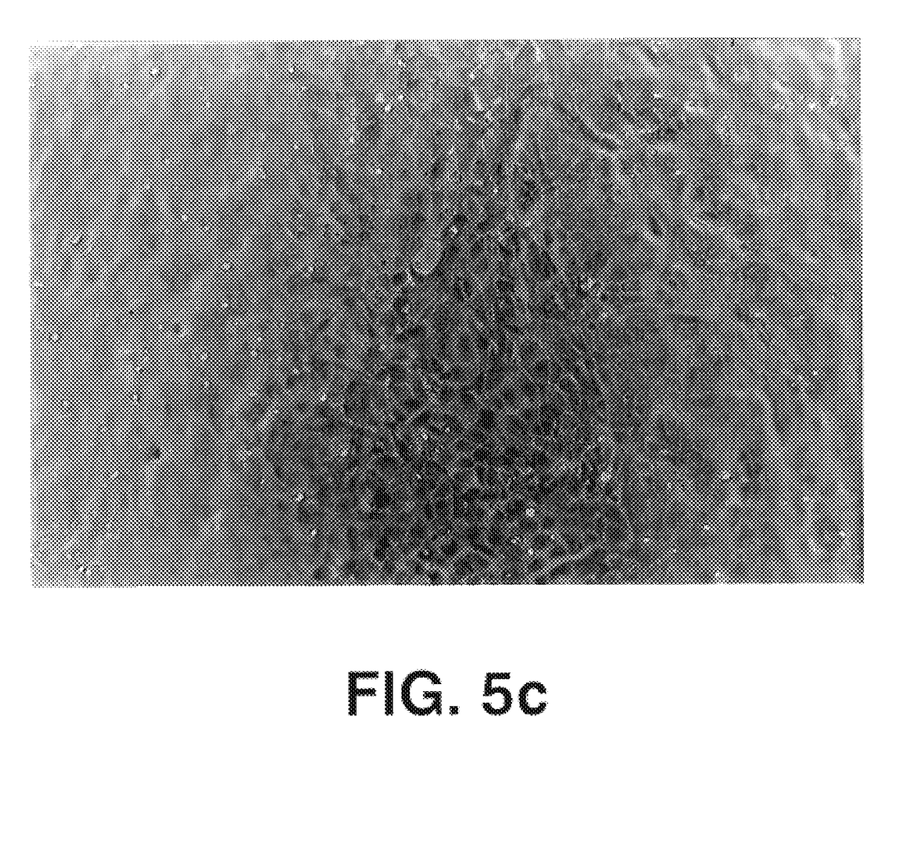

Furthermore, no cytopathogenic effect was seen after infecting the cultures with virus incubated with these SAP concentrations (FIG. 5). Single, scattered cells in the SAP-treated cell cultures showed positive immunofluorescence probably due to adsorption of viral antigen not resulting in virus replication. In the presence of anti-SAP antibodies, there was no effect of SAP, and the results were the same as obtained with the virus-infected control.

In the cell culture system preincubation of SAP with heparin (10 mM) did not abolish SAP's antiviral effect.

Example 3

For electron microscopic investigations of the binding of SAP to influenza A virus SAP molecules were coated with colloidal gold (5 nm) and incubated with virus subtypes for 1 h at 20° C. in the presence of 2 mM $Ca^{++}$. A drop (7 μl) of the mixture was placed on glow-discharged grid with a holey Triafol film (Merck) covered with a thin carbon film. The drop was left on the grid for 15 sec and the grid was flushed with 2% aqueous uranyl acetate, pH 4.2. The specimens were examined in a Zeiss EM 902 electron microscope.

Figure 6A:
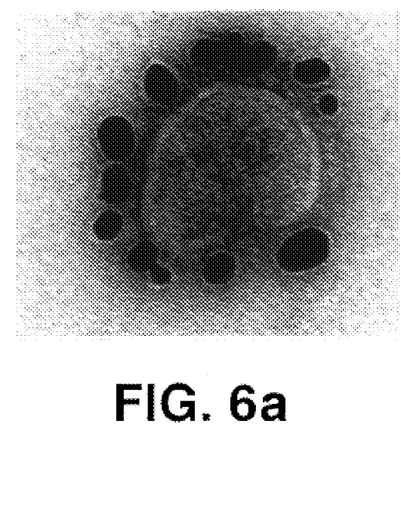
FIG. 6a is an electron micrograph showing the binding of gold-conjugated SAP to the spikes of the viral envelope of influenza A/Shangdong/9/93 ($H_3N_2$) in the presence of 1.2 M $CaCl_2$.
Figure 6B:
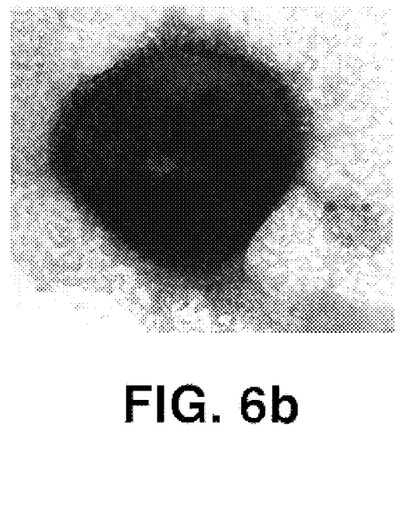
FIG. 6b shows that there was no binding when virus was reacted with gold-conjugated bovine serum albumin.

In $Ca^{++}$-containing medium the gold particles were seen in contact with spikes on the viral envelope (FIG. 6), the degree of coating with the particles varying with the virus strains used. Incubation of virus with gold particles only or with bovine serum albumin coated with colloidal gold showed a random distribution of the gold particles and no selective reactivity with influenza A virions.

Example 4

To illustrate the binding of SAP to influenza A virus subunits SDS-PAGE and Western blotting analyses were performed. SDS-PAGE of A/Shangdong/9/93 and A/Texas/36/91 was performed in 4–20% polyacrylamide gel with discontinuous buffer under reducing and alkylating conditions. The separated viral subunits were electroblotted onto a PVDF-membrane (Immobilon-P, Millipore). The membrane was quenched with TBS containing 0.1% Tween 20 and 0.1% human serum albumin (HSA) and cut into strips. The strips were incubated with 30 to 60 µg SAP in TBS containing 2 mM $Ca^{++}$, washed and blocked with 0.1% HSA and incubated for 1 h at 20° C. with biotinylated rabbit antibodies (1 µg/ml) to SAP. The strips were washed 3 times and alkaline phosphatase-conjugated avidin (1:3000) was added and incubated for 1 h at 20° C. After 3 washes the protein bands were developed with p-nitrophenyl-phosphate (1 mg/ml) in 9.7% diethanolamine, pH 9.6. Controls were performed in parallel with SAP diluted in TBS containing 10 mM EDTA and without addition of SAP.

Figure 7:
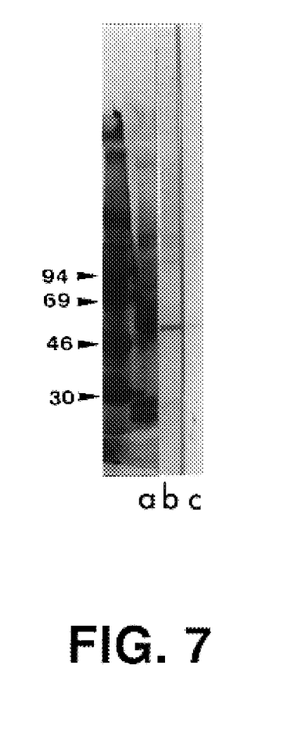
FIG. 7 shows Western blotting analysis of SAP's interaction with influenza A/Shangdong/9/93. a) gold-stained virus preparation, b) strip incubated with SAP in TBS containing 2 mM $CaCl_2$ and c) with SAP in TBS containing 10 mM EDTA. Lane b) shows that SAP exhibits $Ca^{++}$-dependent binding to a viral peptide of 50–55 kDa. Molecular weight standards are shown in margin.

SAP exhibited a $Ca^{++}$-dependent binding to a viral peptide of 50 to 55 kDa (FIG. 7), compatible with the molecular weight of the HA1 polypeptide of the viral hemagglutinin.

References

1. Bristow, C. L. and R. J. Boackle. Mol. Immunol. 23, 1045–1052, 1986.
2. Kubak, B. M. et al. Mol. Immunol. 25, 851–858, 1988.
3. Cathcart, E. S. et al., New Engl. J. Med. 273, 143–146, 1965.
4. Hawkins, P. N. et al. J. Clin. Invest. 86, 1862–1869, 1990.
5. Anderson, J. K. and J. E. Mole. Ann. N.Y. Acad. Sci. 389, 216–234, 1982.
6. Hess et al. Clin. Chim. Acta 173, 331–336, 1988.
7. Loveless, R. W. et al. EMBO J. 11, 813–819, 1992.
8. Hamazaki, H. J. Biol. Chem. 262, 1456–1460, 1987.
9. Nielsen, E. H. et al. APMIS 102, 420–426, 1994.
10. DeBeer, F. C. et al. J. Exp. Med. 154, 1134–1149, 1981.
11. Schwalbe, R. A. et al. J. Biol. Chem. 266, 12896–12901, 1991.
12. Pepys, M. B. et al. Clin. Exp. Immunol. 97, 152–157, 1994.
13. Wilson, I. A. et al. Nature 289, 366, 1981.
14. Couch, R. B. et al. In: Dayton, D. H. et al. (eds). The Secretory Immunologic System. Washington, D.C.: US GPO; 93, 1969.
15. Atkinson, W. L. et al. Arch. Intern. Med. 146, 1751, 1986.
16. Wood, J. and J. Mumford. Vet. Rec. February 8, 126, 1992.
17. Potempa, L. A. et al. J. Biol. Chem. 260, 12142–12147, 1985.
18. Juul Sørensen, I. et al. Int. Arch. Allergy Immunol. 106, 25–31, 1995.
19. DeBeer, F. C. and M. B. Pepys. J. Immunol. Meth. 50, 17–31, 1982.
20. Sørensen, I. J. et al., Scand. J. Immunology 41, 263–267,
21. Gordon, A, Int. Arch. Allergy Immunology 108, 304–308, 1995.
22. Brede, H. D., Int. Arch. Allergy Immunol. 108, 318–320, 1995.
23. von Itzstein et al., Nature 365, 418–423, 1993.
24. Betts, R. F. and Douglas, R. G. In: Mandell, Douglas, Bennett (eds). Principles and practice of infections diseases. 3rd. ed., Churchill Livingstone, 1306–1325, 1990.
25. Webster, R. G., Karger Gazette, no. 57, 1–3, 1993.
26. Herrler, G. et al. Virology 141, 144–147, 1985.
27. Niesters, H. G. M. and van der Zeijst, B. A. M., Microbiol. Sciences 1, 55–58, 1984.
28. Danielsen, B. et al., Biochim. Biophys. Acta, in press, 1997.
29. Painter, R. H., Ann. N.Y. Acad. Sci. 389, 199–215, 1982
30. Dyck, R. F. et al., J. Exp. Med. 152, 1162–1174, 1980
31. Breathnach, S. M. et al., Nature 293, 652–654, 1981
32. Emsley, J. et al., Nature 367, 338–345, 1994
33. Kinoshita, C. M. et al, Protein Sci. 1, 700–709, 1992
34. Pepys, M. B. et al., Lancet 1, 1029–1031, 1977
35. Kubak, B. M. et al., Fed. Proc. 44, 1189, 1985
36. Hamazaki, H., Biochim. Biophys. Acta 998, 231–235, 1989
37. Schwalbe, R. A. et al., J. Biol. Chem. 265, 21749–21762, 1990
38. Brown, M. R. and B. E. Anderson, J. Immunol. 151, 2087–2095, 1993
39. Butler, P. J. G. et al., J. Exp. Med. 172, 13–18, 1990
40. Pepys, M. B. and Butler, P. J. G., Biochem. Biophys. Res. Comm. 148, 308–313, 1987
41. Hind, C. R. K. et al., J. Exp. Med. 159, 1058–1069, 1994
42. Sarlo, K. T., Cell. Immunol. 93, 398–405, 1985
43. Landsmann, P. et al., Eur. J. Biochem. 223, 805–811, 1984
44. Kushner, I., Ann. N.Y. Acad. Sci. 389, 39–45, 1982
45. Williams, E. C. et al., J. Lab. Clin. Med. 120, 159–167, 1992
46. U.S. Pat. No. 5,221,628 A (Northwestern University)

What is claimed is:

1. A pharmaceutical composition for mucosal administration comprising:
   a. a native, synthetic or recombinant serum amyloid P component (SAP) selected from the group consisting of serum amyloid P protein, a subunit of said SAP protein comprising at least one complete SAP polypeptide chain, and a subunit of the SAP polypeptide chain comprising a $Ca^{2+}$-dependent carbohydrate binding site;
   b. $Ca^{2+}$;
   c. a physiologically acceptable carrier; and
   d. a viscosity enhancing factor.

2. The pharmaceutical composition according to claim 1 which is incorporated into a spray or drops.

3. The pharmaceutical composition according to claim 1 wherein the pharmaceutically acceptable carrier comprises an isotonic NaCl solution.

4. The pharmaceutical composition according to claim 1 wherein the $Ca^{2+}$ ions are present in an amount sufficient to (i) enhance the binding of the SAP to a virus or a component thereof and (ii) diminish proteolytic degradation of SAP.

5. The pharmaceutical composition according to claim 4, wherein the $Ca^{2+}$ concentration is from about 1.2 mM to about 2.0 mM, and the $Ca^{2+}$ ions are provided from a soluble Ca-salt.

6. The pharmaceutical composition according to claim 4, wherein the $Ca^{2+}$ concentration is from about 1.2 mM to about 1.5 mM, and the $Ca^{2+}$ ions are provided from a soluble Ca-salt.

7. The pharmaceutical composition of claim 1 wherein the SAP is present in the amount exceeding about 50–100 µg/ml.

8. A kit for the detection and quantitation of SAP binding to influenza virus comprising a container holding SAP in solution, a container holding indicator cells, and a buffer system including $Ca^{2+}$ ions in a concentration of about 1.2 mM to about 2.0 mM.

9. The kit of claim 8 wherein said $Ca^{2+}$ concentration is from about 1.2 mM to about 1.5 mM.

10. A pharmaceutical composition for treating an orthomyxovirus or a paramyxovirus infection, said composition comprising:
   a. a native, synthetic or recombinant serum amyloid P component (SAP) selected from the group consisting of serum amyloid P protein, a subunit of said SAP protein comprising at least one complete SAP polypeptide chain, and a subunit of the SAP polypeptide chain comprising a $Ca^{2+}$-dependent carbohydrate binding site;
   b. $Ca^{2+}$;
   c. a physiologically acceptable carrier; and
   d. a viscosity enhancing factor.

11. The pharmaceutical composition of claim 1, wherein the viral infection is caused by an orthomyxovirus selected from the group consisting of Influenza A virus, Influenza B virus or Influenza C virus.

12. The pharmaceutical composition of claim 1 wherein the viral infection is caused by a paramyxovirus, said paramyxovirus being a parainfluenza virus.

13. A pharmaceutical composition for inhibiting an oxrthomyxovirus or a paramyxovirus infection, said composition comprising:
   a. a native, synthetic or recombinant serum amyloid P component (SAP) selected from the group consisting of serum amyloid P protein, a subunit of said SAP protein comprising at least one complete SAP polypeptide chain, and a subunit of the SAP polypeptide chain comprising a $Ca^{2+}$-dependent carbohydrate binding site;
   b. $Ca^{2+}$;
   c. a physiologically acceptable carrier; and
   d. a viscosity enhancing factor.

14. The pharmaceutical composition of claim 13, wherein the viral infection is caused by an orthomyxovirus selected from the group consisting of Influenza A virus, Influenza B virus or Influenza C virus.

15. The pharmaceutical composition of claim 13 wherein the viral infection is caused by a paramyxovirus, said paramyxovirus being a parainfluenza virus.

* * * * *

UNITED STATES PATENT AND TRADEMARK OFFICE
CERTIFICATE OF CORRECTION

PATENT NO. : 6,406,698 B1
DATED : June 18, 2002
INVENTOR(S) : Sven-Erik Svehag et al.

It is certified that error appears in the above-identified patent and that said Letters Patent is hereby corrected as shown below:

<u>Title page,</u>
Item [75], Inventors, delete "Sven-Erik Svehang" and substitute
-- Sven-Erik Svehag --

Signed and Sealed this

Fifteenth Day of April, 2003

JAMES E. ROGAN
*Director of the United States Patent and Trademark Office*